US012693253B2

(12) United States Patent
Truax

(10) Patent No.: US 12,693,253 B2
(45) Date of Patent: Jul. 28, 2026

(54) FUEL SENSOR

(71) Applicant: Advanced Fuel Dynamics, Inc., Troy, TX (US)

(72) Inventor: Ryan Truax, Troy, TX (US)

(73) Assignee: Advanced Fuel Dynamics, Inc., Troy, TX (US)

( * ) Notice: Subject to any disclaimer, the term of this patent is extended or adjusted under 35 U.S.C. 154(b) by 275 days.

(21) Appl. No.: 18/479,844

(22) Filed: Oct. 3, 2023

(65) Prior Publication Data

US 2024/0118230 A1      Apr. 11, 2024

Related U.S. Application Data

(60) Provisional application No. 63/413,993, filed on Oct. 7, 2022.

(51) Int. Cl.
  *G01N 27/22*        (2006.01)
  *G01N 33/22*        (2006.01)
  *F02D 41/14*        (2006.01)

(52) U.S. Cl.
  CPC ........... *G01N 27/22* (2013.01); *G01N 33/225* (2013.01); *F02D 41/1444* (2013.01)

(58) Field of Classification Search
  CPC . G01N 27/02–24; G01N 33/22; G01N 33/225
  See application file for complete search history.

(56) References Cited

U.S. PATENT DOCUMENTS

| | | | |
|---|---|---|---|
| 4,453,125 A | 6/1984 | Kimura et al. | |
| 5,089,783 A | 2/1992 | Kapsokavathis et al. | |
| 5,150,683 A | 9/1992 | Depa et al. | |

(Continued)

FOREIGN PATENT DOCUMENTS

| | | |
|---|---|---|
| BR | PI0805364 A2 | 8/2010 |
| BR | 102015023180 B1 | 2/2022 |

(Continued)

OTHER PUBLICATIONS

English Translation of EP-2042719-A2 (Year: 2009).*

(Continued)

*Primary Examiner* — Alexander A Mercado
(74) *Attorney, Agent, or Firm* — Luedeka Neely, P.C.; Mark P. Crockett

(57) ABSTRACT

A fuel sensor for a vehicle includes a housing, a fuel composition sensor element disposed within the housing, and two removable and interchangeable fuel connector modules attached to the housing. The fuel composition sensor element comprises an outer cylindrical electrode and an inner cylindrical electrode disposed within and concentric with the outer cylindrical electrode. Both of the fuel connector modules include a flange having a mating surface and an opposing outer surface. The mating surface is configured to removably engage the sensor housing, at either its input side or its output side. Attached to the outer surface of the flange is a fuel connector fitting that is of a standard type configured for connection to a standard fuel connector fitting of the vehicle's fuel system. Use of the removable and interchangeable fuel connector modules eliminates the need for fuel fitting adaptors, thereby reducing the overall size of the sensor.

13 Claims, 4 Drawing Sheets

(56)                    References Cited

U.S. PATENT DOCUMENTS

| | | | |
|---|---|---|---|
| 5,361,035 | A | 11/1994 | Meitzler et al. |
| 5,497,753 | A | 3/1996 | Kopera |
| 7,800,379 | B2 | 9/2010 | Hernandez et al. |
| 7,836,756 | B2 | 11/2010 | Boudaoud et al. |
| 10,816,427 | B2 | 10/2020 | Fernandez Lara et al. |
| 2009/0079445 | A1 | 3/2009 | Lin et al. |
| 2009/0153149 | A1 | 6/2009 | Hernandez et al. |
| 2009/0153154 | A1 | 6/2009 | Hernandez et al. |
| 2010/0229638 | A1 | 9/2010 | Nakamura et al. |
| 2019/0346324 | A1 | 11/2019 | Fernandez Lara et al. |

FOREIGN PATENT DOCUMENTS

| | | | | |
|---|---|---|---|---|
| CA | 2672845 | A1 | 6/2008 | |
| CN | 201773084 | | 3/2011 | |
| DE | 102013205452 | A1 | 7/2014 | |
| EP | 2042719 | A2 * | 4/2009 | ......... F02D 41/0025 |
| JP | 2011179459 | A | 9/2011 | |
| KR | 20090100408 | A | 9/2009 | |
| WO | 2009076504 | A1 | 6/2009 | |
| WO | 2016137343 | A1 | 9/2016 | |

OTHER PUBLICATIONS 2010-2017 Chevrolet Sensor(Replaces Part No. 13577429) 13507129 GMPartsDirect.com, GM Parts Direct Website for Sensor (GM 13507129), Publication Date; Unknown.

Patent Cooperation Treaty, International Searching Authority, International Search Report and Written Opinion for PCT Application No. PCT/US23/75767, Mailing Date: Mar. 1, 2024, Form PCT/ISA/ 220.

* cited by examiner

12 thermistor cavity thermistor cavity

12

26a

26b

24    D1

D2

20a

30

10

FUEL SENSOR

FIELD

This invention relates to the field of automotive technology. More particularly, this invention relates to a fuel composition sensor for flex-fuel vehicles.

BACKGROUND

Fuel composition sensors are commonly used in flex-fuel vehicles to generate an electrical fuel composition signal indicating a ratio of gasoline to alcohol in the fuel blend in the vehicle's fuel tank. This fuel composition signal may be provided to an engine control unit that adjusts various operational characteristics of the engine based on the measured gasoline-to-alcohol ratio. Some current fuel composition sensors also measure the temperature of the fuel to enhance accuracy. This temperature information may also be used by the engine control module.

The fuel composition sensor may be a factory-installed standard component, such as sensors having model numbers 13577394, 13577429, and 13577329 manufactured by GM or others. Alternatively, the fuel composition sensor may be an after-market component.

Currently available fuel composition sensors have various drawbacks as discussed in more detail herein. Preferred embodiments of an improved fuel composition sensor described herein provide several significant advantages over the currently available sensors.

SUMMARY

The above and other needs are met by a fuel sensor for a vehicle that comprises a housing, a fuel composition sensor element disposed within the housing, and two removable and interchangeable fuel connector modules attached to the housing. The housing includes a first surface having a first aperture therein, a second surface having a second aperture therein, and a sensor chamber disposed between the first and second surfaces. The fuel composition sensor element comprises an outer cylindrical electrode and an inner cylindrical electrode disposed within and concentric with the outer cylindrical electrode. The outer electrode has a first inner diameter $D_1$, and the inner cylindrical electrode has a second inner diameter $D_2$. A first electrical contact is electrically connected to the outer cylindrical electrode and a second electrical contact is electrically connected to the inner cylindrical electrode. An outer fluid flow channel is disposed between the outer electrode and the inner electrode, and an inner fluid flow channel is disposed within the inner electrode. The inner flow channel and the outer flow channel form a continuous fluid flow path from the first aperture to the second aperture within the sensor chamber. Both of the fuel connector modules include a flange having a mating surface and an opposing outer surface. The mating surface is configured to removably engage either of the first or second surfaces of the housing. A fuel connector fitting is attached to the outer surface of the flange. The fuel connector fitting is of a standard type that is configured for connection to a standard fuel connector fitting of the vehicle's fuel system. A flange aperture passing through the flange is configured to provide fluid communication between the fuel connector fitting and the first or second aperture in the housing when the flange is engaged with the first or second surface of the housing.

In some embodiments, the first inner diameter $D_1$ is between 20% and 21% larger than the second inner diameter $D_2$.

In some embodiments, the first inner diameter $D_1$ ranges from 0.285 inch to 1.00 inch and the second inner diameter $D_2$ ranges from 0.138 inch to 0.845 inch.

In some embodiments, the first inner diameter $D_1$ is 0.845 inch and the second inner diameter $D_2$ is 0.671 inch.

In some embodiments, the outer cylindrical electrode and the inner cylindrical electrode each have a length ranging from 0.25 inch to 2.50 inch.

In some embodiments, the length of the outer cylindrical electrode and the inner cylindrical electrode is 1.0 inch.

In some embodiments, the first inner diameter $D_1$ ranges between 84% and 85% of the length of the outer cylindrical electrode.

In some embodiments, the second inner diameter $D_2$ ranges between 67% and 68% of the length of the inner cylindrical electrode.

In some embodiments, the fuel sensor includes a fuel pressure sensor attached to the housing. The fuel pressure sensor is operable to generate a fuel pressure signal indicative of pressure of fuel flowing through the sensor chamber.

In some embodiments, the fuel sensor includes a thermistor attached to the housing. The thermistor is operable to generate a fuel temperature signal indicative of temperature of fuel flowing through the sensor chamber.

In some embodiments, the fuel connector fitting comprises a standard type of fitting selected from the group consisting of 5/16-inch, 3/8-inch, 1/2-inch quick-connect, A/N, DIN, pipe, and O-ring boss of various sizing ranging from −4 to −12 or equivalent.

In some embodiments, the fuel sensor includes two O-ring connector gaskets, each configured to provide a fluid seal between the flange of one of the fuel connector modules and the first or second surface of the housing to which the flange is engaged.

In some embodiments, the fuel sensor of claim 1 includes an oscillator circuit, a fuel pressure sensor, and a microprocessor. The oscillator circuit, which is connected to the first and second electrical contacts of the fuel composition sensor element, is operable to generate a frequency signal based on dielectric properties of fuel flowing through the outer flow channel. The fuel pressure sensor is operable to generate a fuel pressure signal indicative of pressure of fuel flowing through the sensor chamber. Based on the frequency signal, the microprocessor generates a fuel composition signal, and based the fuel pressure signal, the microprocessor determines whether the fuel composition signal is inaccurate because of a loss of fuel pressure or because of presence of air in the outer fuel channel due to abnormal operation of the vehicle's fuel system.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Figure 1:
FIG. 1 depicts an exploded view of a fuel sensor according to an embodiment of the invention.
Figures 2A, 2B:
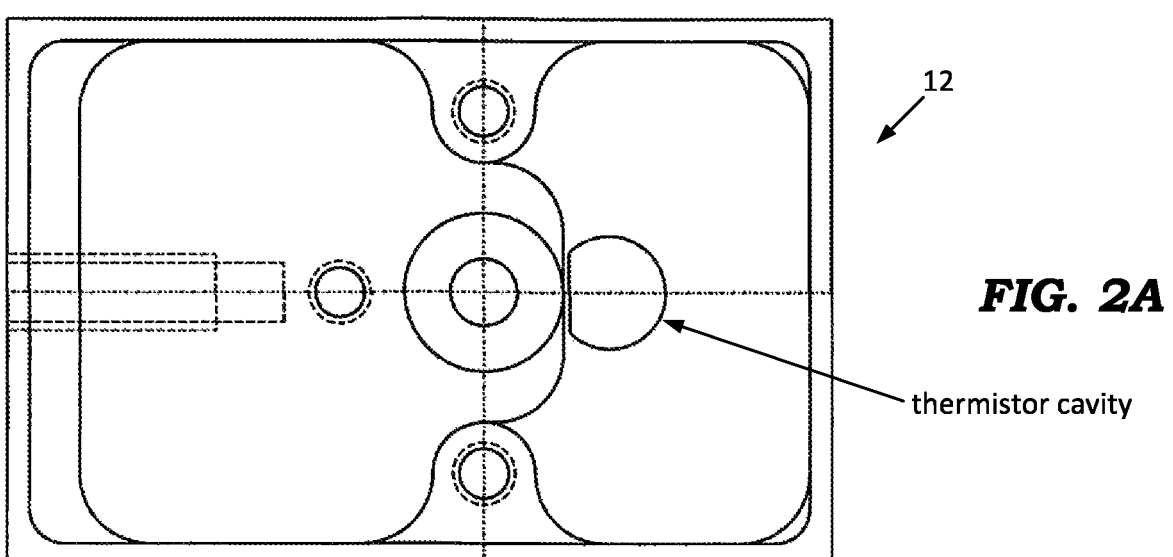
FIGS. 2A and 2B depict a top view and a side view of the fuel sensor according to an embodiment of the invention.
Figure 3:
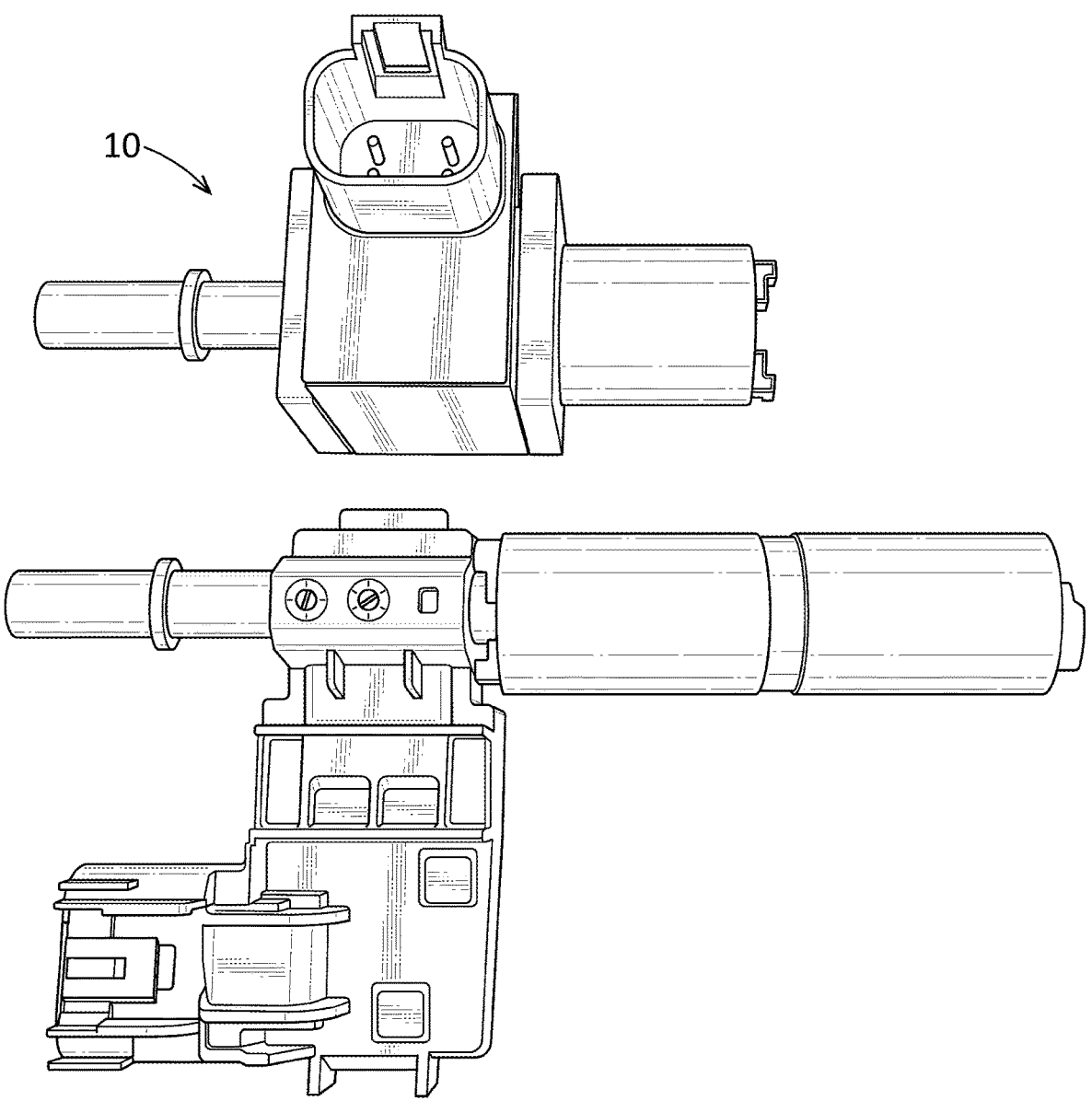
FIG. 3 depicts a comparison of the physical footprints of a conventional fuel sensor and the fuel sensor according to an embodiment of the invention.

Described herein is an improved fuel composition sensor 10, embodiments of which are depicted in FIGS. 1-4. FIG. 1 depicts an exploded view of a preferred embodiment of the fuel sensor 10 that includes a housing 12, a fuel composition sensor element 14, two fuel connector modules 16a-16b, and two O-ring gaskets 18a-18b. The housing 12 has opposing first and second surfaces 20a-20b, each having a central circular aperture 22a-22b. A cylindrical sensor chamber 24 is disposed between the first and second surfaces 20a-20b within the housing 12, such that the first aperture 22a, the sensor chamber 24, and the second aperture 22b are in fluid communication.

The fuel composition sensor element 14 comprises a cylindrical capacitor that fits within the cylindrical chamber 24 in the housing 12. The sensor element 14 includes outer and inner cylindrical electrodes 26a-26b. The inner electrode 26b is disposed within the outer electrode 26a such that a channel 30 is formed between them. A spacer element 28 maintains the proper spacing between the outer and inner cylindrical electrodes 26a-26b.

The capacitance between the two electrodes 26a-26b changes based on the ethanol content of the fuel blend flowing in the channel 30. The change in capacitance affects the oscillation frequency of an AC electrical signal generated by an oscillator 32 that is monitored by a microprocessor 34, both of which are disposed on a PC board in the sensor housing 12 (see FIG. 4). As described in more detail hereinafter, the microprocessor 34 calculates a fuel composition value based at least in part on the frequency of an AC electrical signal generated by an oscillator 32. The fuel composition value is provided to the vehicle's engine control unit via a connector 50 attached to the housing 12.

The outer electrode 26a has an inner diameter $D_1$ and the inner electrode 26b has an inner diameter $D_2$. In a preferred embodiment, $D_1$ is about 0.845 inch and $D_2$ is about 0.671 inch, although the diameters may range from about 0.295 to 1.0 inch and from about 0.140 to 0.845 inch in other embodiments. Thus, in a preferred embodiment, $D_1$ is 20% to 21% larger than $D_2$. The lengths L1 and L2 of the electrodes 26a-26b are about 1.0 inch in a preferred embodiment, although their lengths may range from about 0.25 to 2.50 inch in other embodiments. Thus, in preferred embodiments, $D_1$ is about 84% to 85% of the length L1 of the outer electrode 26a, and $D_2$ is about 67% to 68% of the length L2 of the inner electrode 26b. The fuel composition sensor element 14 includes electrical contacts 30a and 30b that are electrically connected to the outer and inner electrodes, respectively.

A significant advantage of the fuel sensor 10 is that the sensor element 14 has a significantly larger fuel flow area than conventional fuel composition sensors because of the larger diameters of the electrodes 26a-26b. For comparison, the inner electrode of a conventional capacitive fuel sensor has an inner diameter of about 0.133 inch, and its outer electrode has an inner diameter of about 0.285 inch. The conventional sensor is designed for engines generating less than 300 horsepower (hp), and it cannot provide sufficient fuel flow for performance car engines that generate 300 hp or more. The larger flow area of the fuel composition sensor element 14 described herein solves this problem of insufficient fuel delivery for performance cars, without being restrictive up to about 2000 hp. The larger fuel flow surface area also provides a larger sensing surface area for higher accuracy.

Preferred embodiments provide unrestricted fuel flow through the sensor 10, thus reducing turbulence. This is accomplished by sizing the diameter D2 of the inner electrode 26b to be larger than the diameter of the aperture 42 of the flange 36. In contrast, prior sensor designs required all fuel passing through the sensor to be forced through and around an inner electrode having an inner diameter that is smaller than the diameter of the fuel fitting aperture. Thus, preferred embodiments of the sensor 10 provide a significant improvement over the prior sensor designs by reducing obstructions in the path of the fuel flow, thereby reducing turbulence, heat generation from the restriction, and cavitation in high-flow applications.

As shown in FIG. 1, the removable and interchangeable fuel connector modules 16a-16b each include a flange 36 having a mating surface 38 that is configured to engage either of the first or second surfaces 20a-20b of the housing 12. Each flange 36 has an outer surface 40 opposing the mating surface 38, and a flange aperture 42 passing through the flange 36. A fuel connector fitting 44 is integrated into the outer surface 40 of the flange 36. In preferred embodiments, the fuel connector fitting 44 is a standard type fitting that is configured to mate to standard fuel connector fittings of vehicle fuel systems. FIG. 1 depicts various types of standard fittings 44 that may be provided on various fuel connector modules 16a-16b, the choice of which depends on the configuration of the fuel system of the particular vehicle in which the fuel sensor 10 is to be installed. From left to right, the fittings 44 shown in FIG. 1 include Quick Connect, A/N, ORB, Pipe, Barb, and DIN, each of which may be provided in various applicable sizes. It will be appreciated that other types of fittings 44 may be provided in alternative embodiments.

The fuel sensor 10 described herein may be installed as part of an after-market conversion kit for a vehicle that has no fuel composition sensor because the vehicle was not originally designed to run on a gas/ethanol blend, gas/methanol blend, or other type of fuel. The sensor 10 may also be provided as OEM components in flex-fuel vehicles. The vehicle's fuel line input/output connection points for such installations typically include one male and one female connector. There are several different types of fuel line fittings in various vehicles, such as quick-connect, A/N, DIN, pipe, and O-ring boss. These fittings may be male or female, and there may be different sizes for each. For example, some conventional fuel composition sensors have a ⅜-inch male quick-connect fitting on each end for connecting to the vehicle's fuel lines.

Preferred embodiments of the fuel sensor 10 described herein may be provided to a customer with any combination of several available connector fittings 44 on the fuel connector modules 16a-16b, including the standard ⅜-inch fittings and many other types of connections as described above. The removable and replaceable fuel connector modules 16a-16b allow the type and size of connector fitting that is compatible with the vehicle to be attached directly to the sensor housing 12 for easy installation into the vehicle, eliminating the need for the adaptors required by conventional fuel composition sensors. This is a significant advantage in terms of space savings. For example, one current after-market sensor (shown on the bottom in FIG. 3) is almost four inches long without any adapters added. In comparison, the housing 12 of the fuel sensor 10 described herein is approximately one inch long, and it is shipped to the customer with the correct fuel connector modules 16a-16b installed so that it requires no adapters. The total length of the fuel sensor 10 with the connector modules 16a-16b attached is less than about three inches (shown on the top in FIG. 3), which makes it much easier to package within the vehicle or fixture on which it is installed. The fuel sensor 10 should also be less expensive because a customer will be able to select the appropriate fitting configuration when ordering, thereby eliminating the need for adaptors that would increase the overall cost.

As shown in FIG. 1, the O-ring gaskets 18a-18b provide a seal between the first and second surfaces 20a-20b housing 12 and the mating surfaces 38 of the interchangeable fuel connector modules 16a-16b to prevent leakage of fuel. In alternative embodiments, sealing/gasket structures other than O-rings may be used.

Figure 4:
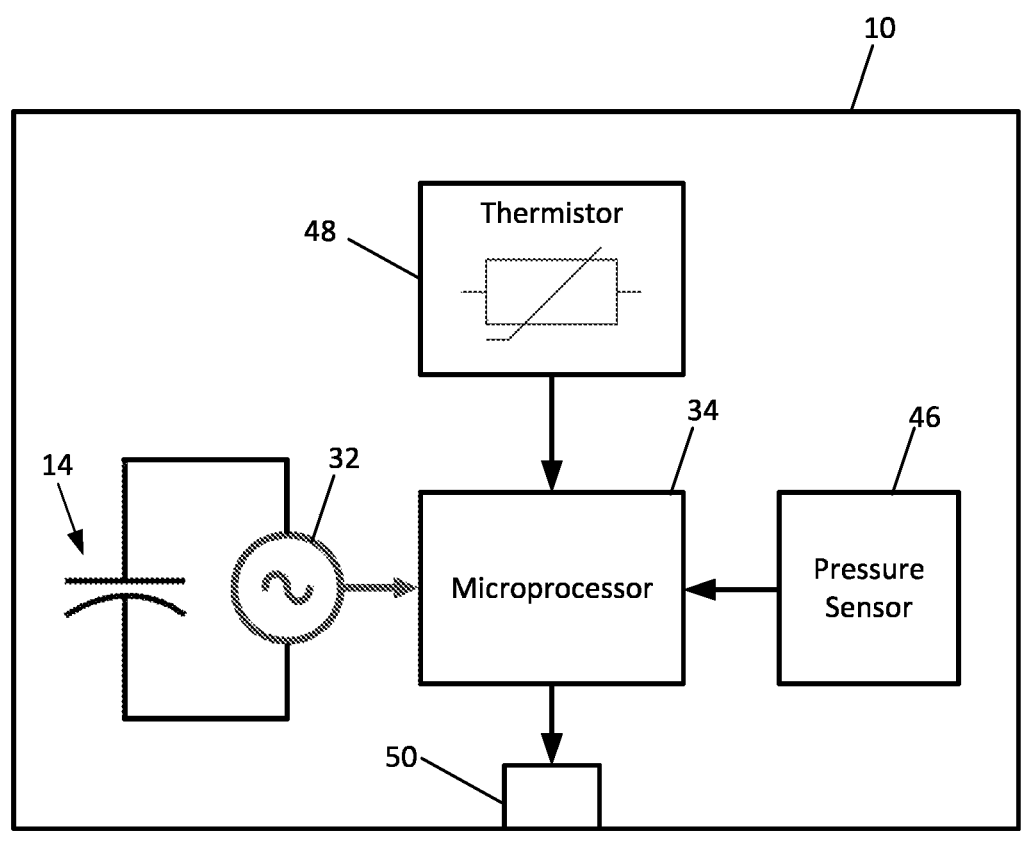
FIG. 4 depicts a functional block diagram of the fuel sensor according to an embodiment of the invention.

As shown in FIG. 4, preferred embodiments of the fuel sensor 10 include a pressure sensor 46 that generates a fuel pressure signal. The microprocessor 34 uses the fuel pressure signal as a check to verify that the fuel composition signal generated by the fuel composition sensor element 14 is correct. In a conventional fuel composition sensor, if no fuel is flowing through its sensor element, the fuel composition signal will drop to zero, which can cause engine damage if the fuel content is actually a high blend of ethanol. A preferred embodiment of the fuel sensor 10 described herein solves this problem by including the pressure sensor 46 to measure the fuel pressure to verify that the fuel content reading is accurate, and to ensure it is not affected by a loss of fuel pressure or by the presence of air in the fuel line due to abnormal operation of the fuel system.

Although the preferred embodiment of the fuel sensor 10 includes the measurement of fuel pressure, it is not a requirement in all applications. In high performance applications, fuel pressure can be used as a safety check to limit performance if the fuel pressure drops below what is required. Also, in simpler systems a fuel pressure measurement can be used for a pressure gauge or as a data logger to record pressure data.

As shown in FIG. 4, preferred embodiments of the fuel sensor 10 also include a thermistor 48 that generates a fuel temperature signal. The thermistor 48 is located on the PC board and is disposed in the thermistor cavity shown in FIGS. 2A and 2B. Because relative permittivity of the fuel can vary with temperature, the fuel temperature signal is used as an offset in the calculation of the fuel composition signal.

In summary, various embodiments of the improved fuel sensor described herein provide several advantages for aftermarket applications, including:

Ease of installation due to a compact housing design, low-profile fuel connection fittings, and a shorter overall length compared to conventional fuel content sensors;

Ease of installation due to modular fittings with a wide range of available connector types and sizes, thereby eliminating the need for adaptors;

Larger sensor element area that provides for a higher rate of fuel flow for performance and high horsepower needs—up to 16 times the fuel flow rate of a conventional fuel content sensor;

Larger sensor element that provides higher accuracy than prior fuel sensors;

Integrated fuel pressure sensor ensures fuel composition output signal is accurate;

Elimination of need for a bypass line in high flow fuel systems;

Hardened electronics incorporating reliable, OE quality components;

Ease of adaption to conventional harness connector;

Reduction in fuel turbulence and friction-induced heat transfer caused by flow restriction;

Signal outputs for fuel content, fuel temperature and fuel pressure; and

Billet housings in some embodiments, and housings formed using lower-cost manufacturing methods in other embodiments.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A fuel sensor for a vehicle, comprising:

a housing comprising:

a first surface having a first aperture therein;

a second surface opposing the first surface, the second surface having a second aperture therein; and a sensor chamber disposed between the first and second surfaces, wherein the first aperture, the sensor chamber, and the second aperture are in fluid communication;

a fuel composition sensor element disposed within the sensor chamber, the fuel composition sensor element comprising:

an outer cylindrical electrode having a first inner diameter $D_1$;

an inner cylindrical electrode disposed within and concentric with the outer cylindrical electrode, the inner cylindrical electrode having a second inner diameter $D_2$;

a first electrical contact electrically connected to the outer cylindrical electrode;

a second electrical contact electrically connected to the inner cylindrical electrode;

an outer fluid flow channel disposed between the outer cylindrical electrode and the inner cylindrical electrode; and an inner fluid flow channel disposed within the inner cylindrical electrode, wherein the inner flow channel and the outer flow channel form a continuous fluid flow path from the first aperture to the second aperture within the sensor chamber;

at least two fuel connector modules that are removable and interchangeable, each fuel connector module comprising:

a flange having a mating surface configured to removably engage either of the first or second surfaces of the housing, and an outer surface opposing the mating surface;

a fuel connector fitting attached to the outer surface of the flange, the fuel connector fitting selected from the group consisting of a ⅜-inch quick-connect fitting, an A/N fitting, a DIN fitting, a pipe fitting, and an O-ring boss fitting; and a flange aperture passing through the flange, the flange aperture configured to provide fluid communication between the fuel connector fitting and the first or second aperture in the housing when the flange is engaged with the first or second surface of the housing;

an oscillator circuit attached to the housing and connected to the first and second electrical contacts of the fuel composition sensor element, the oscillator circuit operable to generate a frequency signal based on dielectric properties of fuel flowing through the outer flow channel;

a fuel pressure sensor attached to the housing, the fuel pressure sensor operable to generate a fuel pressure signal indicative of pressure of fuel flowing through the sensor chamber; and a microprocessor attached to the housing, the microprocessor operable to receive the frequency signal and the fuel pressure signal and:

generate a fuel composition signal based at least in part on the frequency signal, determine based on the fuel pressure signal that there is a loss of fuel pressure, and determine based on the loss of fuel pressure that the fuel composition signal is inaccurate.

2. The fuel sensor of claim 1 wherein the first inner diameter $D_1$ is between 20% and 21% larger than the second inner diameter $D_2$.

3. The fuel sensor of claim 1 wherein the first inner diameter $D_1$ ranges from 0.285 inch to 1.00 inch and the second inner diameter $D_2$ ranges from 0.138 inch to 0.845 inch.

4. The fuel sensor of claim 1 wherein the first inner diameter $D_1$ is 0.845 inch and the second inner diameter $D_2$ is 0.671 inch.

5. The fuel sensor of claim 1 wherein the second inner diameter $D_2$ is larger than the flange aperture.

6. The fuel sensor of claim 1 wherein the outer cylindrical electrode and the inner cylindrical electrode each have a length ranging from 0.25 inch to 2.50 inch.

7. The fuel sensor of claim 6 wherein the length of the outer cylindrical electrode and the inner cylindrical electrode is 1.0 inch.

8. The fuel sensor of claim 6 wherein the first inner diameter $D_1$ ranges between 84% and 85% of the length of the outer cylindrical electrode.

9. The fuel sensor of claim 6 wherein the second inner diameter $D_2$ ranges between 67% and 68% of the length of the inner cylindrical electrode.

10. The fuel sensor of claim 1 further comprising a fuel pressure sensor attached to the housing, the fuel pressure sensor operable to generate a fuel pressure signal indicative of pressure of fuel flowing through the sensor chamber.

11. The fuel sensor of claim 1 further comprising a thermistor attached to the housing, the thermistor operable to generate a fuel temperature signal indicative of temperature of fuel flowing through the sensor chamber.

12. The fuel sensor of claim 1 further comprising at least two O-ring connector gaskets, each configured to provide a fluid seal between the flange of one of the fuel connector modules and the first or second surface of the housing to which the flange is engaged.

13. A fuel sensor for a vehicle, comprising:

a housing having a sensor chamber;

a fuel composition sensor element disposed within the sensor chamber, the fuel composition sensor element comprising:

an outer cylindrical electrode;

an inner cylindrical electrode disposed within and concentric with the outer cylindrical electrode;

a first electrical contact electrically connected to the outer cylindrical electrode;

a second electrical contact electrically connected to the inner cylindrical electrode;

an outer fluid flow channel disposed between the outer cylindrical electrode and the inner cylindrical electrode; and an inner fluid flow channel disposed within the inner cylindrical electrode, wherein the inner flow channel and the outer flow channel form a continuous fluid flow path from the first aperture to the second aperture within the sensor chamber;

an oscillator circuit attached to the housing and connected to the first and second electrical contacts of the fuel composition sensor element, the oscillator circuit operable to generate a frequency signal based on dielectric properties of fuel flowing through the outer flow channel;

a fuel pressure sensor attached to the housing, the fuel pressure sensor operable to generate a fuel pressure signal indicative of pressure of fuel flowing through the sensor chamber;

a microprocessor attached to the housing, the microprocessor operable to receive the frequency signal and the fuel pressure signal and:

generate a fuel composition signal based at least in part on the frequency signal, determine based on the fuel pressure signal that there is a loss of fuel pressure, and determine based on the loss of fuel pressure that the fuel composition signal is inaccurate; and input and output fuel connector fittings attached to the housing.

* * * * *